United States Patent
Gao et al.

(10) Patent No.: US 9,289,553 B2
(45) Date of Patent: Mar. 22, 2016

(54) BONE MARROW ASPIRATION DEVICE

(71) Applicant: SpineSmith Partners, L.P., Austin, TX (US)

(72) Inventors: Jizong Gao, Cedar Park, TX (US); Michelle Kelly, Austin, TX (US); John B. Rossman, Austin, TX (US); Michael Landry, Austin, TX (US)

(73) Assignee: SpineSmith Partners, L.P., Austin, TX (US)

( * ) Notice: Subject to any disclaimer, the term of this patent is extended or adjusted under 35 U.S.C. 154(b) by 237 days.

(21) Appl. No.: 14/061,635

(22) Filed: Oct. 23, 2013

(65) Prior Publication Data

US 2014/0114285 A1   Apr. 24, 2014

Related U.S. Application Data

(60) Provisional application No. 61/717,504, filed on Oct. 23, 2012.

(51) Int. Cl.

| | |
|---|---|
| *A61M 5/19* | (2006.01) |
| *A61M 1/00* | (2006.01) |
| *A61M 39/24* | (2006.01) |
| *A61M 5/31* | (2006.01) |
| *A61M 5/20* | (2006.01) |
| *A61B 10/02* | (2006.01) |
| *A61M 5/178* | (2006.01) |
| *A61M 1/02* | (2006.01) |

(52) U.S. Cl.
CPC . *A61M 5/19* (2013.01); *A61M 1/00* (2013.01); *A61M 1/0009* (2013.01); *A61M 5/204* (2013.01); *A61M 5/3129* (2013.01); *A61M 39/24* (2013.01); *A61B 10/025* (2013.01); *A61B 10/0283* (2013.01); *A61B 2010/0258* (2013.01); *A61M 1/0272* (2013.01); *A61M 5/178* (2013.01); *A61M 2202/10* (2013.01)

(58) Field of Classification Search
CPC ....... A61M 5/19; A61M 5/178; A61M 39/24; A61M 2202/10; A61B 10/025; A61B 10/0283; A61B 2010/0258
See application file for complete search history.

(56) References Cited

U.S. PATENT DOCUMENTS

| | | | | |
|---|---|---|---|---|
| 5,318,782 A | * | 6/1994 | Weis-Fogh | 424/529 |
| 6,702,760 B2 | * | 3/2004 | Krause et al. | 600/564 |
| 2003/0208181 A1 | * | 11/2003 | Geise et al. | 604/406 |

* cited by examiner

*Primary Examiner* — Devin Henson
(74) *Attorney, Agent, or Firm* — Winstead PC

(57) ABSTRACT

An embodiment of the invention is directed to a bone marrow aspiration device comprising a plurality of syringes, each of which operates in a series of sequential steps to obtain bone marrow of high quality and therapeutic value, i.e., having a high MSC/ml number. An embodiment of the invention preferably comprises three syringes, wherein a first syringe is used to aspirate bone marrow from a subject, a second syringe contains an anticoagulant, and the third syringe contains a mixture of the bone marrow aspirate and the anticoagulant.

3 Claims, 5 Drawing Sheets

BONE MARROW ASPIRATION DEVICE

CROSS-REFERENCES TO RELATED APPLICATIONS

This application claims the benefit under 35 U.S.C. §119(e) of U.S. Provisional Patent Application No. 61/717,504 filed Oct. 23, 2012, which is incorporated herein by reference in its entirety as if fully set forth herein.

BACKGROUND OF THE INVENTION

During bone marrow aspiration, a needle is injected into the cancellous bone. A syringe is connected to the needle to aspirate the bone marrow. It is known that the first rapid forceful pull of the syringe plunger is essential to the quality of bone marrow aspirate. However, different operators may apply different pulling force to the plunger and therefore inconsistent bone marrow aspiration is a concern. Aspirating bone marrow from the iliac crest using small volumes of 1-4 ml has been historically proposed for harvesting adult mesenchymal stem cells and described as a standard technique to avoid blood dilution. Studies have shown that bone marrow aspiration using a larger volume syringe (50 ml) as compared with a smaller volume syringe (10 ml) results in a reduced mesenchymal stem cell count in bone marrow aspirates. The current invention provides an apparatus that applies a rapid pulling force to the plunger, reducing use/user variances while also allowing for a more consistent quality of aspirated bone marrow by maximizing mesenchymal stem cell content.

SUMMARY OF THE INVENTION

An embodiment of the invention is directed to a bone marrow aspiration device comprising a plurality of syringes, each of which operates in a series of sequential steps to obtain bone marrow of high quality and therapeutic value, i.e., having a high MSC/ml number. An embodiment of the invention preferably comprises three syringes, wherein a first syringe is used to aspirate bone marrow from a subject, a second syringe contains an anticoagulant, and the third syringe contains a mixture of the bone marrow aspirate and the anticoagulant. Another embodiment of the invention is directed to a method for using the bone marrow aspiration device as set forth herein.

DETAILED DESCRIPTION OF EXEMPLARY EMBODIMENTS

Figure 1:
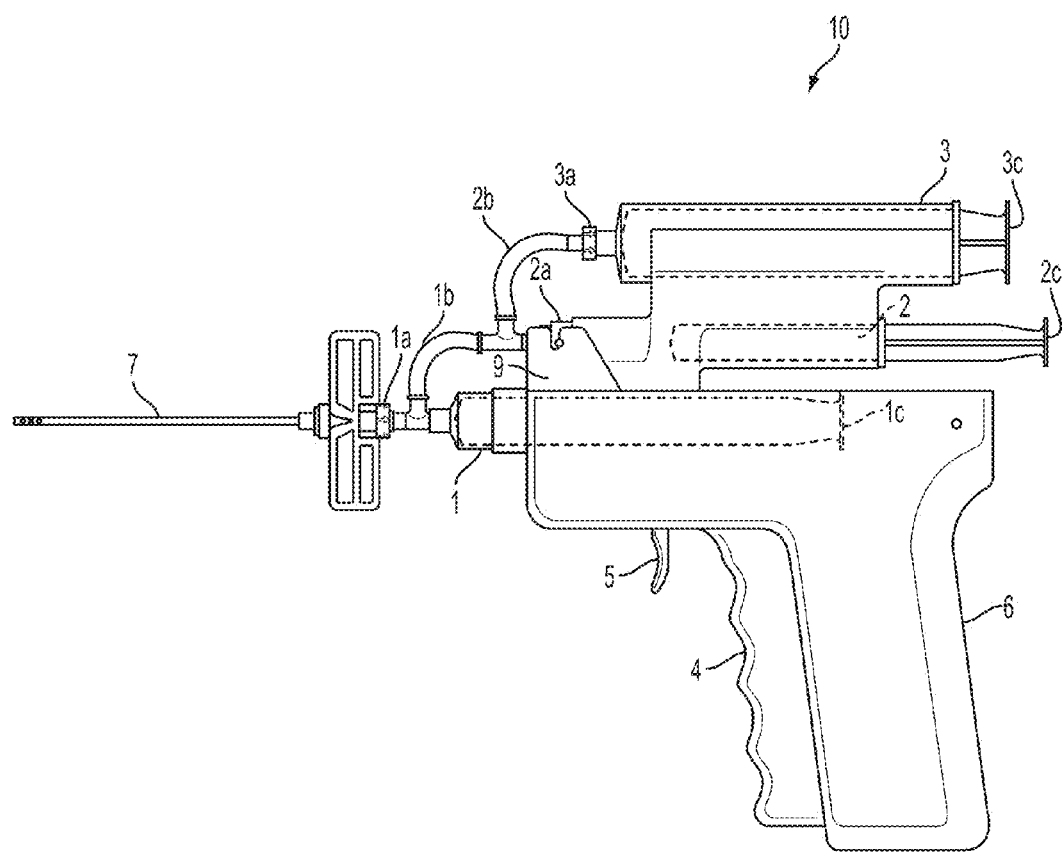
FIG. 1 is directed to a bone marrow aspiration device in accordance with an embodiment of the invention.

The advantages of the claimed invention include: streamlining bone marrow collection by reducing use/user variances; providing a rapid pull to improve the bone marrow aspirate quality and stem cell content; and assisting the operator for multiple bone marrow collections.

An embodiment of the invention is an apparatus that is designed to assist the operator in aspirating bone marrow. The apparatus comprises a plurality of syringes. The apparatus employs at least one "trigger" mechanism that allows the user to control when aspiration begins. In certain embodiments, the design includes multiple triggers at different positions that allow for various forces and speeds of aspiration, depending on the user's preference.

The viscosity of bone marrow is 37.5-400 cPs. Using a 10 cc syringe at 30° C., the bone marrow flow rate is approximately 3-5 cc/sec when pulling the syringe plunger with a force of 60 N (Newtons). The ideal bone marrow flow rate during bone marrow collection (a rapid pull) is 5-10 cc/sec based on expert opinion. The key metric in a bone marrow aspirate sample is mesenchymal stem cell per milliliter (MSC/mL). Studies have shown that aspiration of a smaller volume of bone marrow than the total volume of a syringe pulled results in higher MSC/mL. For example, experiments conducted by Hernigou et al. on a test group of normal adults showed that the maximum MSC number (mean 2,062±1552) was obtained with an aspiration of 1 ml with a 10-ml syringe and the minimum MSC number (mean 95±8) was obtained with an aspiration of 50 ml with a 50-ml syringe. Additionally, the ease of drawing a small syringe allows greater transmission of force during aspiration. Both of these factors point to the preferred use of a syringe with a smaller volume than a syringe with a larger volume. Furthermore, studies have shown that repeated application of vacuum prevents in-flow of peripheral blood into the aspirate which has a relatively low MSC/mL when compared to bone marrow. Thus, instead of a single aspiration site with a single syringe of large volume, a plurality of aspiration sites with repeated aspirations is recommended. The study by Hernigou et al. also concludes that aspiration of only 10% of the full syringe volume resulted in a greater MSC concentration compared to syringes filled with progressively higher percentages of the full volume for either syringe size.

An embodiment of the invention is directed to a bone marrow aspiration device comprising a plurality of syringes, each of which operates in a series of sequential steps to obtain bone marrow of high quality and therapeutic value, i.e., having a high MSC/ml number. An embodiment of the invention preferably comprises three syringes, wherein a first syringe is used to aspirate bone marrow from a subject, a second syringe contains an anticoagulant, and the third syringe contains a mixture of the bone marrow aspirate and the anticoagulant.

An embodiment of the invention is directed to a method for extracting bone marrow from a subject comprising the steps of: providing a bone marrow aspiration device comprising: a first syringe, a second syringe and a third syringe, wherein the first syringe is connected to a needle and comprises a first one-way valve between the needle and the first syringe that directs the flow of fluid solely into the first syringe and wherein the first syringe is connected to the second syringe by a first tubing; and wherein the second syringe comprises a second one-way valve that directs the flow of fluid solely out of the second syringe and wherein the second syringe is connected to the third syringe by a second tubing, and wherein the second syringe contains an anticoagulant material; and further wherein the third syringe comprises a third one-way valve that directs the flow of fluid solely into the second syringe; inserting the needle into the bone of a subject; creating a vacuum in the first syringe sufficient to withdraw bone marrow from the subject; filling a portion of the volume of the first syringe with the subject's bone marrow; releasing the bone marrow from the first syringe into the first tubing; releasing a portion of the anticoagulant material contained within the second syringe into first tubing and second tubing; combining the anticoagulant material and the bone marrow in the second tubing to form a mixture; and transferring the mixture to the third syringe for storage.

In an embodiment of the invention, one or more of the syringes of the device are connected to one another by tubing. The tubing that connects the syringes of the device is coupled to one or more valves that regulate the directionality of flow of fluids through the tubing and/or the syringes. In an embodiment of the invention, the syringe that is used to aspirate bone marrow from a subject (aspiration syringe) is connected to a needle having fenestrations at its tip. In certain embodiments, the needle that is a connected to the aspiration syringe is a Jamshidi needle.

In embodiment of the invention, the movement of one or more of the syringes is controlled by a control arm. In certain embodiments, the directional positioning and movement of one or more of the syringes is controlled by the movement of a syringe rack.

In an embodiment of the invention, the device comprises a primary trigger that is capable of controlling one or more the syringes of the device. In a further embodiment of the invention, the device comprises a secondary trigger that is capable of controlling one or more syringes of the device. In certain embodiments of the invention, the movement and positioning of the primary trigger and secondary trigger causes the up and down movement of a trigger pin.

In some embodiments of the invention, the primary trigger and secondary trigger control the movement and position of the control arm and syringe rack through the use of compression springs connected to the primary trigger.

Now referring to FIG. 1, a bone marrow aspiration device 10 is shown. The device comprises a first syringe 1, a second syringe 2 and a third syringe 3. The first syringe is housed within a handle 6. The handle comprises a primary trigger 4 and a secondary trigger 5. The first syringe is connected to a needle 7 such as a Jamshidi needle. The Jamshidi needle is inserted into the subject's bone to aspirate bone marrow (not shown). A one-way valve 1a is inserted between the needle and the first syringe to regulate the direction of flow of the bone marrow aspirate. When in use, the bone marrow aspirate is withdrawn from the subject and flows into the first syringe when the plunger of the first syringe is drawn out to create a vacuum. The unidirectional flow of the bone marrow aspirate from the subject bone into the first syringe is controlled by the one-way valve, which ensures that there is no back-flow of bone marrow aspirate into the subject (see part 1a in FIG. 3 and arrows showing direction of flow of aspirate into syringe 1). The first syringe is connected by tubing 1b to the second syringe. The control arm 9 and syringe rack 11 (see FIG. 2) control the movement of the aspiration syringe.

Figure 2:
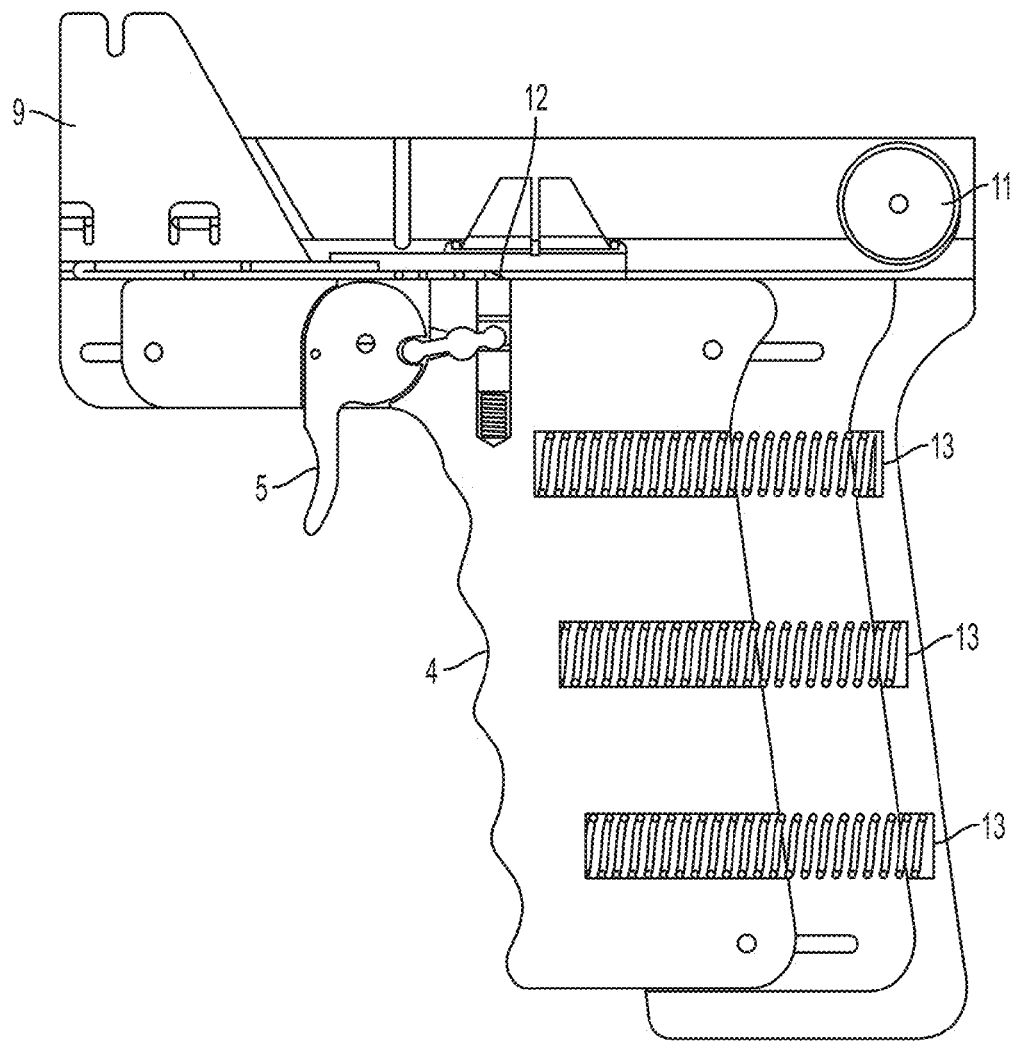
FIG. 2 is directed to a portion of the bone marrow aspiration device in accordance with an embodiment of the invention.

As seen in FIG. 2, which depicts the device 10 without the syringes, the positions of the primary trigger 4 and secondary trigger 5 are controlled by a plurality of compression springs 13. The secondary trigger 5 controls the up and down movement of a trigger pin 12.

Figure 3:
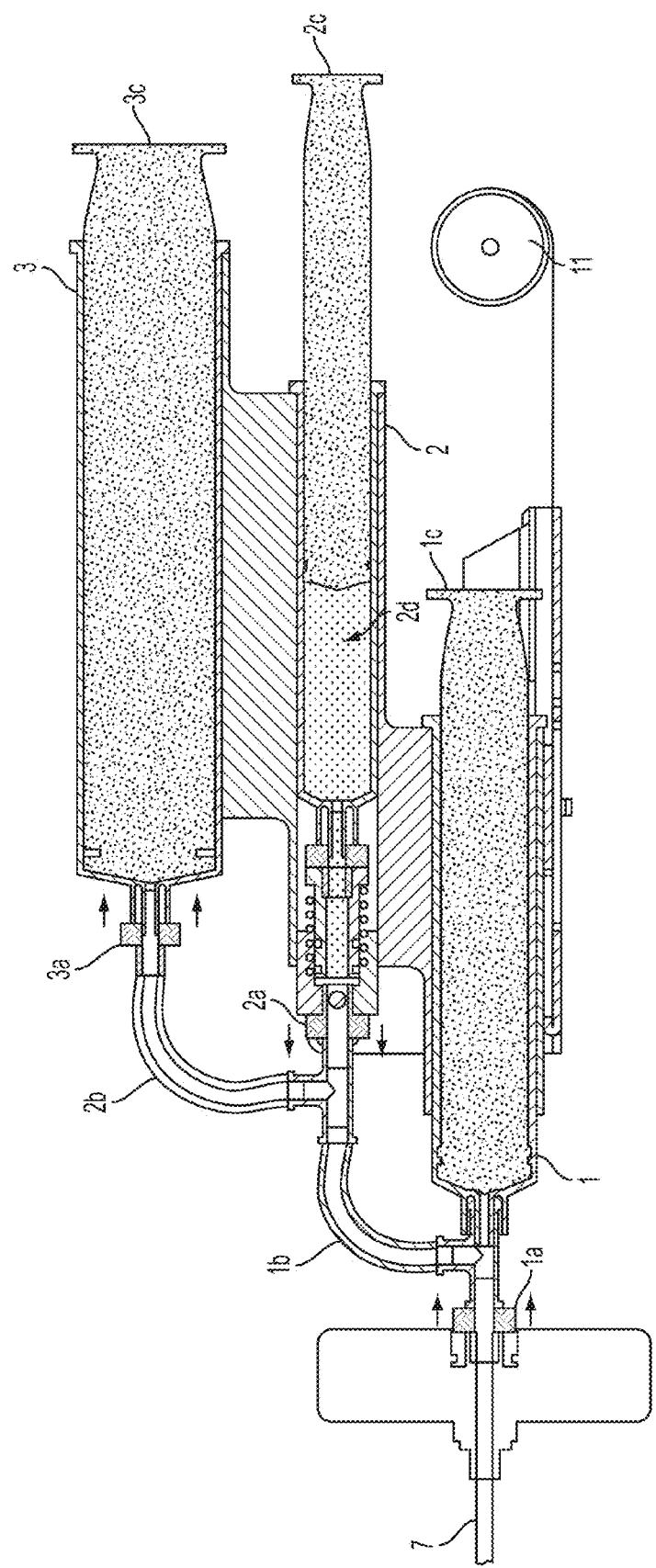
FIG. 3 shows the arrangement of the syringes in accordance with an embodiment of the invention.

As set forth in FIG. 3, the second syringe 2 contains an anticoagulant 2d. In certain embodiments, the anticoagulant is ACD-A (Anticoagulant Citrate Dextrose Solution, Solution A). In other embodiments, the anticoagulant is heparin. As shown in FIG. 3, the second syringe 2 comprises a one-way valve 2a, which only permits flow of the anticoagulant out of the syringe and prevents any backflow into the syringe as indicated by the arrow. The second syringe is connected by tubing 2b to the third syringe.

Figure 4:
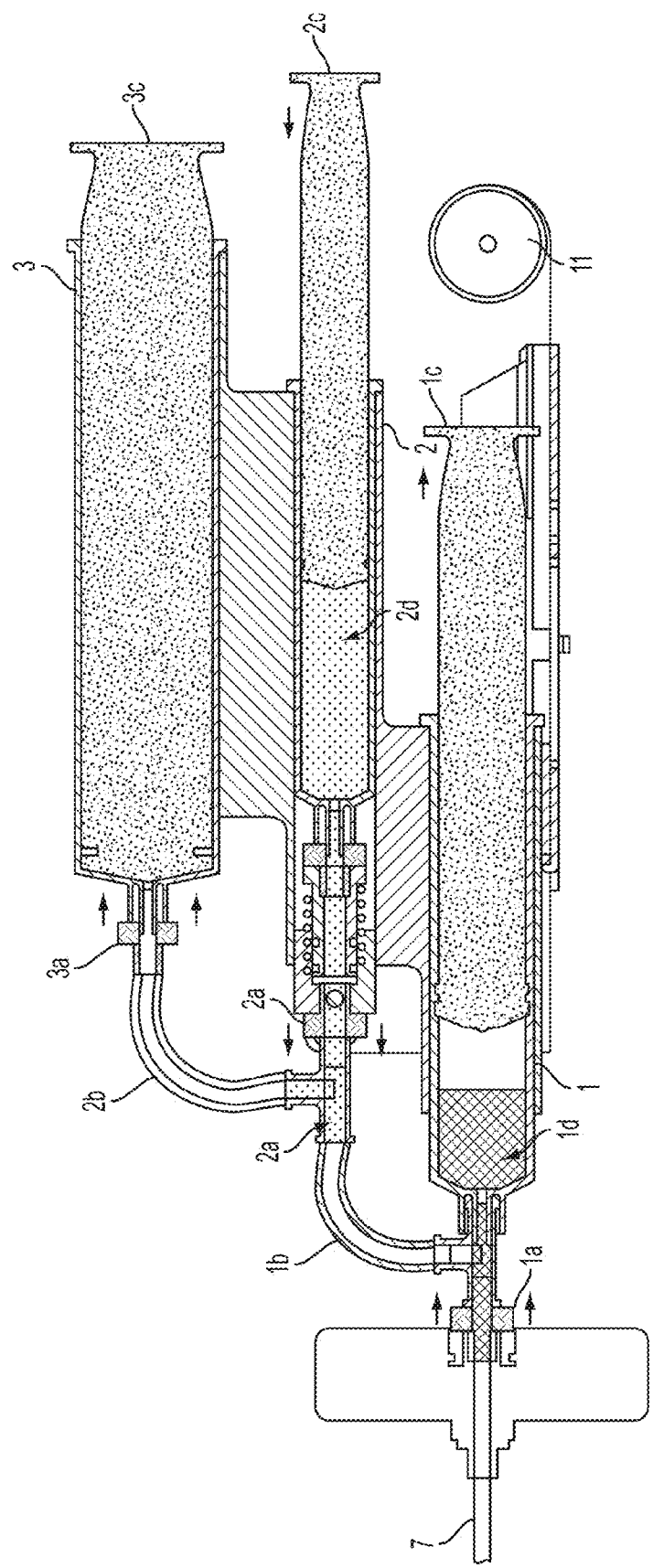
FIG. 4 shows the arrangement of the syringes in accordance with an embodiment of the invention.

As shown in FIG. 4, the third syringe 3 (reservoir syringe) comprises a one-way valve 3a that permits the unidirectional flow of fluid into the third syringe and prevents the flow of fluid out of the third syringe. Through the positioning of the one-way valves, the proper and directional flow of fluids within the syringes of the bone marrow aspiration device is ensured.

Figure 5:
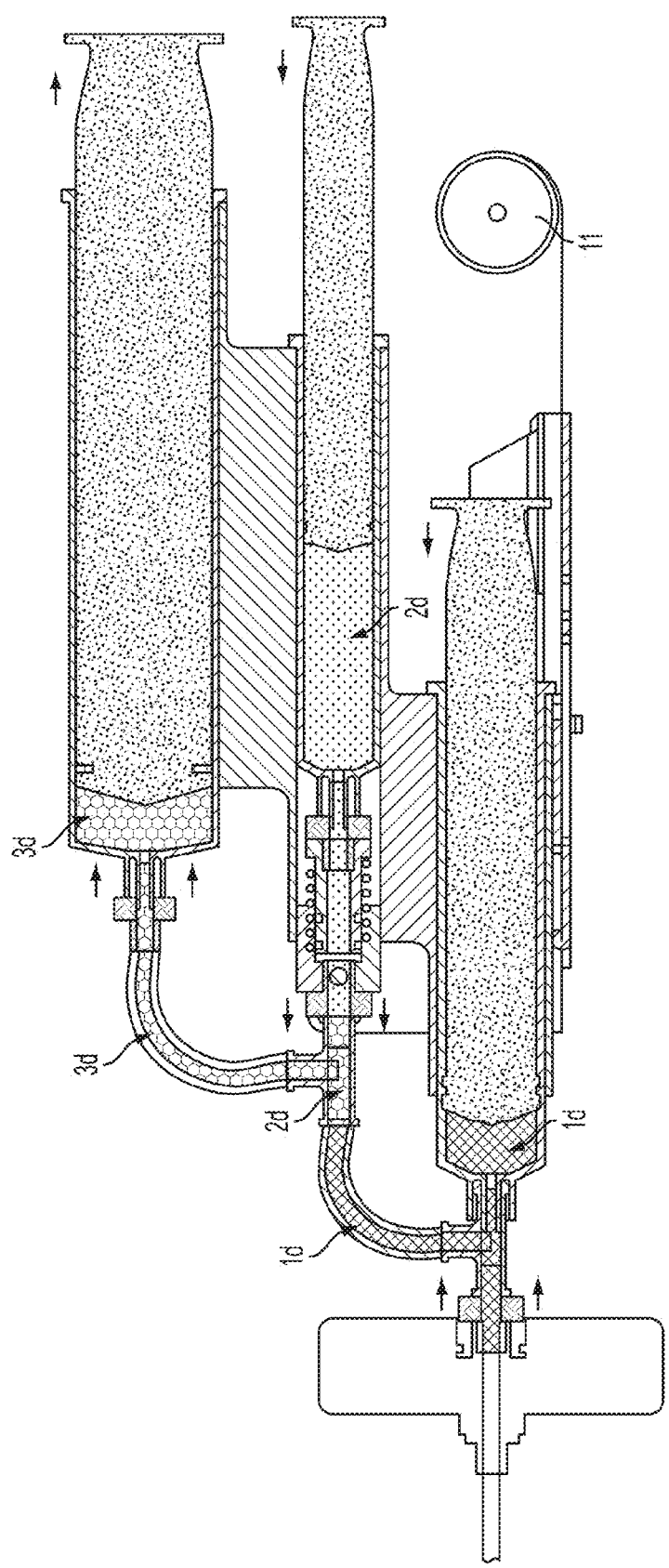
FIG. 5 shows the arrangement of the syringes in accordance with an embodiment of the invention.

The claimed device 10 operates to withdraw bone marrow aspirate from a subject. The operation of the device is set forth in FIGS. 3, 4 and 5. FIG. 3 shows the device at the starting position. In the starting position, the plunger 1c of the first syringe 1 is fully recessed within the body of the syringe. The second syringe 2 is partially filled with anticoagulant. The plunger 3c of the third syringe 3 is fully recessed within the body of the syringe In the starting position, the primary trigger is located in a forward position as shown in FIG. 2, i.e., with the compression springs extended. The syringe rack 11 and the control arm 9 are both in the forward position. The trigger pin 12 is in the up position when the device is in the starting position.

When the device is ready to be used in the aspiration step, the secondary trigger 5 is pulled back, which causes the trigger pin 12 to move down. The downward movement of the trigger pin 12 permits the control arm 9 and syringe rack 11 to be pulled back. In the aspiration step (FIG. 4), the plunger 1c of the aspiration syringe 1 is pulled back to create a hard vacuum. Bone marrow 1d is aspirated into the aspiration syringe 1 such that a portion of the volume of the aspiration syringe 1 is filled with bone marrow as shown in FIG. 4. In an embodiment of the invention, the volume of the syringe that is filled with bone marrow is between 10% to 50% of the volume of the syringe.

Following the aspiration step, the bone marrow collected in the aspiration syringe is transferred to the reservoir (third) syringe. In the transfer step (FIG. 5), the syringe rack 11 and control arm 9 are pulled forward. The primary trigger 4 is moved backward and the trigger pin 12 moves upward. In the transfer step, the plunger 1c of the aspiration syringe 1 and the plunger 2c of the anticoagulant syringe 2 are pushed inward into the barrel of the respective syringes, which causes the bone marrow aspirate 1d and the anticoagulant 2d to mix within tubing 2b to form an aspirate-anticoagulant mixture 3d, which is transferred into the reservoir syringe for storage and future use.

Following the transfer step, the device is returned to the starting position with the primary trigger 4 in a forward position, the control arm 9 and syringe rack 11 in a forward position and the trigger pin 12 in an upward position. Once the device has returned to the starting position, it can be used to repeat the steps of the bone marrow aspiration process.

An embodiment of the invention is directed to a method for aspirating bone marrow from a subject comprising the steps of aspirating the bone marrow from a subject, mixing the bone marrow with an anticoagulant and mixing the bone marrow and anticoagulant in a reservoir for further storage.

In the preceding detailed description, the invention is described with reference to specific exemplary embodiments thereof and locations of use within the spine. Various modifications and changes may be made thereto without departing from the broader spirit and scope of the invention as set forth in the claims. The specification and drawings are, accordingly, to be regarded in an illustrative rather than a restrictive sense.

The invention claimed is:

1. A bone marrow aspiration device comprising:
   a first syringe coupled to a slideable control arm, and further being in fluid communication with a needle, and further comprising a first one-way valve between the needle and the first syringe that directs a flow of a first fluid solely into the first syringe, and wherein the first syringe is connected to a second syringe by a first tubing;

wherein the second syringe comprises a second one-way valve that directs a flow of a second fluid solely out of the second syringe, and wherein the second syringe is connected to a third syringe by a second tubing; and wherein the third syringe that comprises a third one-way valve that directs the flow of the first and second fluids solely into the third syringe.

2. The device of claim 1 further comprising:

a primary trigger;

a secondary trigger; and a trigger pin coupled to the secondary trigger, and wherein the trigger pin disengages the control arm when the secondary trigger is actuated.

3. A method for extracting bone marrow from a subject comprising the steps of:

providing a bone marrow aspiration device comprising: a first syringe, coupled to a slideable control arm, and further being in fluid communication with a needle, and further comprising a first one-way valve between the needle and the first syringe that directs a flow of a first fluid solely into the first syringe, and wherein the first syringe is connected to a second syringe by a first tubing;

wherein the second syringe comprises a second one-way valve that directs a flow of a second fluid solely out of the second syringe and wherein the second syringe is connected to a third syringe by a second tubing, and wherein the second fluid comprises an anticoagulant material; and wherein the third syringe comprises a third one-way valve that directs the flow of the first and second fluids solely into the third syringe;

inserting the needle into a bone of a subject;

creating a vacuum in the first syringe sufficient to withdraw bone marrow from the subject;

filling a portion of the volume of the first syringe with the subject's bone marrow;

releasing the bone marrow from the first syringe into the first tubing;

releasing a portion of the anticoagulant material contained within the second syringe into first tubing and second tubing;

combining the anticoagulant material and the bone marrow in the second tubing to form a mixture; and transferring the mixture to the third syringe for storage.

* * * * *